United States Patent [19]

Fukukawa et al.

[11] Patent Number: 4,613,666
[45] Date of Patent: Sep. 23, 1986

[54] NEPLANOCIN A DERIVATIVES

[75] Inventors: Kiyofumi Fukukawa, Sapporo; Takao Hirano; Masatoshi Tsujino, both of Shizuoka; Tooru Ueda, Sapporo; Tadashiro Fujii; Satoshi Yaginuma, both of Shizuoka, all of Japan

[73] Assignee: Toyo Jozo Kabushiki Kaisha, Shizuoka, Japan

[21] Appl. No.: 776,093

[22] Filed: Sep. 16, 1985

Related U.S. Application Data

[63] Continuation of Ser. No. 330,696, Dec. 14, 1981, abandoned.

[30] Foreign Application Priority Data

Dec. 12, 1980 [JP] Japan .................. 55-176401
Dec. 19, 1980 [JP] Japan .................. 55-178825
Nov. 18, 1981 [JP] Japan .................. 56-185100

[51] Int. Cl.$^4$ .................................. C07D 473/32
[52] U.S. Cl. ............................. 544/277; 435/122
[58] Field of Search ............... 544/244, 265, 277

[56] References Cited

U.S. PATENT DOCUMENTS

| | | | |
|---|---|---|---|
| 4,138,562 | 2/1979 | Vince .................. | 544/277 |
| 4,268,672 | 5/1981 | Vince .................. | 544/265 |
| 4,321,376 | 3/1982 | Otani et al. ........... | 544/277 |
| 4,345,078 | 8/1982 | Hofer et al. .......... | 544/244 |
| 4,423,218 | 12/1983 | Otani et al. ........... | 544/277 |

OTHER PUBLICATIONS

Chemical Abstracts, Tenth Collective Index, vols. 86–95, 1977–1981, pp. 17437–17438.
Ohgi et al., Chemical Abstracts, vol. 88(23), Abst. No. 170,420w, Jun. 5, 1978.

*Primary Examiner*—Alan L. Rotman
*Attorney, Agent, or Firm*—Young & Thompson

[57] ABSTRACT

Neplanocin A derivatives of the formula

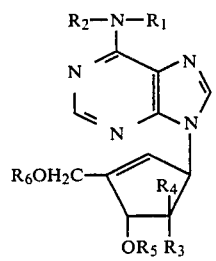

wherein $R_1$ and $R_2$ are hydrogen or benzoyl, $R_3$ is hydrogen or $OR_8$, $R_5$ is hydrogen or acetyl, $R_6$ is hydrogen, acetyl or benzoyl, when $R_3$ is hydrogen, $R_4$ is hydrogen or halogen, hydroxy, acetoxy, acetylthio, amino or azide, and when $R_3$ is $OR_8$, $R_4$ is hydrogen, $R_8$ is hydrogen or acetyl, or $R_8$ and $R_5$ together form benzylidene, and at least one of $R_8$, $R_5$ and $R_6$ is other than hydrogen. The compounds of the present invention have inhibitory action for the growth of L 5178 Y cells and have the same or superior activity as neplanocin A, and hence are useful as antitumor agents.

4 Claims, No Drawings

NEPLANOCIN A DERIVATIVES

This application is a continuation of application Ser. No. 330,696, filed Dec. 14, 1981, now abandoned.

This invention relates to novel neplanocin A derivatives. More particularly, the present invention relates to neplanocin A derivatives of the formula

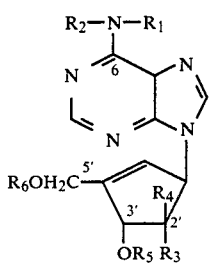

wherein $R_1$ and $R_2$ are hydrogen or benzoyl, $R_3$ is hydrogen or $OR_8$, $R_5$ is hydrogen or acetyl, $R_6$ is hydrogen, acetyl or benzoyl, when $R_3$ is hydrogen, $R_4$ is hydrogen or halogen, hydroxy, acetoxy, acetylthio, amino or azide, and when $R_3$ is $OR_8$, $R_4$ is hydrogen, $R_8$ is hydrogen or acetyl, or $R_8$ and $R_5$ together form benzylidene, and at least one of $R_8$, $R_5$ and $R_6$ is other than hydrogen.

Neplanocin A, originally designated as antibiotic A 11079-Blb, is an antibiotic produced by Ampullariella sp. A 11079 FERM-P No. 4494 having antitumor activity and inhibitory action for plant pathogenic fungi (U.S. application Ser. No. 18,790, filed Mar. 8, 1979 and its continuing application Ser. No. 205,350 filed Nov. 3, 1980 and Japan Pat. Open. No. 54-154792). According to the results of instrumental analysis and the similarity of this antibiotic to aristeromycin [J. Chem. Soc. Chem. Comm., 852–853 (1967), Chem. Pharm. Bull., 20(5), 940–946 (1972)], the neplanocin is a nucleoside antibiotic-related substance, having a cyclopentene ring, of the formula

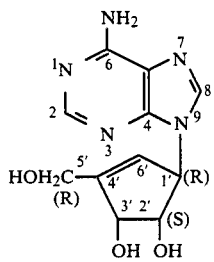

[refer to Current Chemotherapy and Infectious Disease, 1558–1559 (1980)] and has an absolute configuration of 1'(R), 2'(R) and 3'(R). [Nucleic Acids Research, Symposium Series, No. 8, S 65–S 67 (1980)].

The compounds [I] of the present invention have an inhibitory action for the growth of L 5178 Y cells and have the same or superior activity as neplanocin A.

In the present invention, if the amine group at position-6 of adenine ring is not substituted, an acid addition salt can be made. Therefore, the pharmaceutically acceptable acid addition salts are within the scope of the present invention. Such a salt is a pharmacologically acceptable non-toxic salt, and can be an inorganic salt such as sulfate, hydrochloride or phosphate, or an organic salt such as acetate, propionate, maleate, tartrate, citrate or salt of an amino acid.

The nomenclature of the compounds of the present invention and their intermediates is given according to the position numbers of formula [II] above.

Processes for the production of compound [I] of the present invention are as follows:

(1) A compound [I] wherein $R_1$ and $R_2$ are hydrogen, $R_3$ is $OR_8$, $R_4$ is hydrogen and $R_8$, $R_5$ and $R_6$ are acetyl, i.e. 2', 3', 5'-triacetyl neplanocin A, can be synthesized by acetylation of neplanocin A. Acetylation can be performed by reaction with acetic anhydride in the presence of a tertiary organic amine such as pyridine, N-methylmorpholine or dimethylaniline.

(2) A compound [I], wherein $R_1$, $R_2$ and $R_6$ are hydrogen, $R_3$ is $OR_8$, $R_4$ is hydrogen and $R_8$ and $R_5$ together are benzylidene, i.e. 2', 3'-O-benzylidene neplanocin A, can be synthesized by benzylidenation of neplanocin A. Benzylidenation can be performed by reacting with benzaldehyde in the presence of zinc chloride.

(3) A compound [I], wherein $R_1$, $R_2$ and $R_6$ are benzoyl, $R_3$ is $OR_8$ and $R_8$ and $R_5$ are hydrogen, i.e. $N^6$, $N^6$, 5'-O-tribenzoyl neplanocin A, can be synthesized by protecting a hydroxy group at positions-2' and -3' of neplanocin A with a protective group and benzoylating the thus-obtained 2', 3'-O-protected-neplanocin A to prepare $N^6$, $N^6$-5'-O-tribenzoyl-2', 3'-O-protective group neplanocin A.

The above protective groups for the 2'- or 3'-hydroxy group are conventional protective groups commonly used in nucleic acid chemistry, and are, for example, an aldehyde compound residue which forms acetal together with two vicinal oxygen atoms, or a ketone compound residue which forms ketal. Examples of the said protective groups are isopropylidene, methoxymethylene, ethoxymethylene, ethoxyethylidene or benzylidene. These protective groups can be introduced by reacting with the corresponding aldehyde or ketone in the presence of an acid catalyst. Isopropylidene can be introduced by reacting with acetone or 2,2-dimethoxypropane in the presence of a Lewis acid such as hydrochloric acid, hydrogen chloride, hydrogen bromide, perchloric acid, zinc chloride, p-toluene sulfonic acid or di-p-nitrophenyl phosphoric acid.

Methoxymethylene, ethoxymethylene and ethoxyethylidene can be introduced by reacting with an excess of orthoformic or orthoacetic acid ester in the presence of hydrogen chloride or p-toluenesulfonic acid in dimethylformamide. Benzylidene can be introduced by reacting with benzaldehyde in the presence of an acid catalyst such as zinc chloride, hydrogen chloride or $BF_3$-etherate.

Benzoylation can be performed by reacting an at least three molar excess of a benzoyl halide such as benzoyl chloride in the presence of a tertiary organic amine such as pyridine, N-methylmorpholine or dimethylaniline.

The 2',3'-O-protective group of the thus-obtained $N^6,N^6,5'$-O-tribenzoyl-2',3'-O-protected-neplanocin A can be removed by any known method for the removal of a 2',3'-O-protective group, for example by treating with an acidic solvent such as aqueous formic acid or acetic acid.

(4) A compound [I] wherein $R_1$ and $R_6$ are benzoyl, $R_3$ is $OR_8$, and $R_8$ and $R_5$ are hydrogen, i.e. $N_6,5'$-O-dibenzyl neplanocin A, can be produced by removing the 2',3'-O-protective group of $N^6$, $N_6,5'$-O-tribenzoyl-2',3'-O-substituted-neplanocin A hereinabove, removing the monobenzoyl group or removing the 2',3'-O-protective group after removal of the monobenzoyl group.

The monobenzoyl group can be removed by treating with N-bromosuccinimide in an organic solvent or with aqueous ammonia in a lower alcohol. Removal of 2',3'-O-protective group can be performed as hereinbefore explained.

(5) A compound [I] wherein $R_1$ is hydrogen or benzoyl, $R_2$, $R_3$, $R_5$ and $R_6$ are hydrogen and $R_4$ is acetoxy, i.e. a compound of the formula

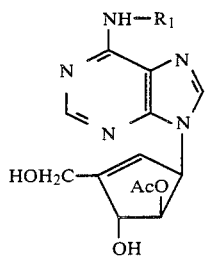

[A1]

wherein $R_1$ has the same meaning as hereinabove and Ac is acetyl, can be synthesized by protecting the hydroxyl group at positions 3' and 5' of a compound of the formula

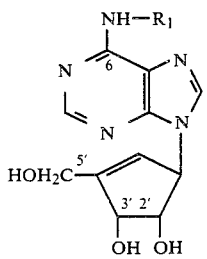

[2]

wherein $R_1$ has the same meaning as hereinabove, with 1,1,3,3-tetraisopropyl disiloxane-1,3-di-yl to obtain a compound of the formula

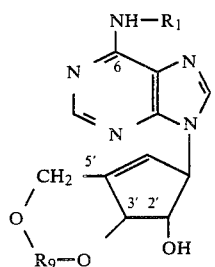

[3]

wherein $R_9$ is —Si(i—Pro)$_2$—O—Si(i—Pro)$_2$—, i—Pro is isopropyl and $R_1$ has the same meaning as hereinabove, trifluoromethansulfonylating the hydroxy group at position 2' of the said compound to obtain the intermediate of the formula

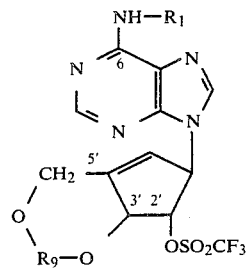

[4]

wherein $R_1$ and $R_5$ have the same meanings as hereinabove, reacting this intermediate with alkali metal acetate to obtain an intermediate of the formula

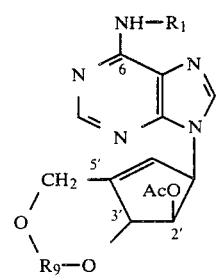

[5]

wherein $R_1$, Ac and $R_9$ have the same meanings hereinabove, and removing the 3',5'-O-protective group by treating with tetrabutylammonium fluoride.

A starting material [2] wherein $R_1$ is benzoyl, i.e. $N^6$-benzoyl neplanocin A, is produced by reacting neplanocin A with a benzoylation reagent in the presence of a tertiary organic amine to obtain a benzoylated compound of the formula

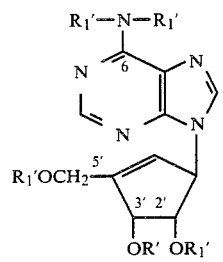

[1]

wherein $R_1'$ is benzoyl, and treating the thus-obtained compound with alkali hydroxide. An example of the benzoylation reagent is conventionally benzoyl chloride. Benzoylation can be performed in the presence of a tertiary organic amine such as pyridine, N-methylmorpholine or dimethylaniline. The benzyl groups, except the one at position $N^6$, are removed by treating compound [1] with alkali hydroxide.

The protection of the hydroxy groups at positions 3' and 5' of compound [2] can preferably be effected with 1,1,3,3-tetraisopropyl disiloxane-1,3-di-yl. The introduction of this protective group is described in J. Chem. Res., (1979), 24–25, 181–197. Other protective groups used in the field of saccharide and nucleic acid chemistry can be used.

The thus-obtained compound [3] can be isolated because it is stable in water due to the existing disiloxazinyl group in compound (3).

Trifluoromethane sulfonylation of the hydroxy group at position 2' of compound [3] can be effected by reacting with a trifluoromethane sulfonylhalide such as trifluoromethane sulfonyl chloride in the presence of a tertiary organic amine such as triethylamine or pyridine in an organic solvent. 4-dimethylaminopyridine is preferably added for promotion of the reaction.

Compound [5] is obtained by reacting the thus-obtained compound [4] with an alkali metal acetate in an organic solvent such as hexamethylphosphoramide. Examples of alkali metal acetate are sodium acetate, potassium acetate and lithium acetate. The reaction proceeds at room temperature and requires no heat unless it proceeds too slowly.

Removal of the 3',3'-O-protective group in compound [5] can easily be effected by treating with tetrabutylammonium fluoride in an organic solvent. Examples of organic solvents are tetrahydrofurance and dioxane. The reaction proceeds at room temperature in a short time.

Isolation and purification of the compound [A1] can be effected as hereinafter explained.

(6) A compound wherein $R_1$ is hydrogen or benzoyl, $R_4$ is acetylthio, and $R_2$, $R_3$, $R_5$ and $R_6$ are hydrogen, i.e. a compound of the formula

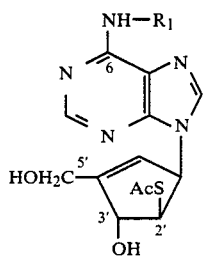

[A2]

wherein Ac is acetyl, is produced by reacting compound [4] with an alkali metal thioacetate to obtain a compound of the formula

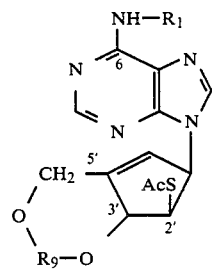

[6]

wherein $R_9$ is —Si(i—Pro)$_2$—O—Si(i—Pro)$_2$—, iPro is isopropyl and $R_1$ and Ac have the same meanings as hereinbefore, and removing the 3',5'-O-protective group by tetrabutylammonium fluoride.

Examples of alkali metal thioacetate are sodium thioacetate, potassium thioacetate and lithium thioacetate. The reaction of compound [4] and an alkali metal thioacetate, and the removal of the 3',5'-O-protective group in compound [6], are performed by the same procedure as in (5) above.

The thus-obtained compound [A2] can be isolated and purified as explained hereinafter.

(7) A compound, wherein $R_1$ is hydrogen or benzoyl, $R_4$ is halogen, $R_2$, $R_3$, $R_5$ and $R_6$ are hydrogen, i.e. a compound of the formula

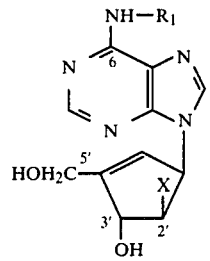

[A3]

wherein $R_1$ is hydrogen or benzoyl and X is halogen, is produced by reacting compound [4] with alkali halogenide of the formula

MX wherein X is halogen and M is a reactive alkali metal atom, in an organic solvent to obtain a compound of the formula

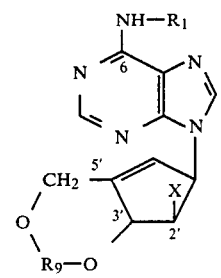

[7]

wherein $R_9$ is —Si(i—Pro)$_2$—O—Si(i—Pro)$_2$—, i—Pro is isopropyl, and $R_1$ and X have the same meanings as hereinbefore, and removing the 3',5'-O-protective group with tetrabutyl ammonium fluoride.

Examples of alkali halide as halogenating reagent having reactivity for 2'-halogenation of compound [4] are LiF, LiCl, LiBr, LiI and NaI.

An example of an organic solvent for the above halogenation is hexamethylphosphoramide. The halogenation can be conducted at room temperature and hence it is not necessary to heat unless the reaction rate is too slow.

The removal of the 3',5'-O-protective group in compound [7] can be effected by the same process as explained in (1) hereinbefore.

Compound [A3] can be purified by the process hereinafter explained. (8) A compound wherein $R_1$ is hydrogen or benzoyl, $R_4$ is azide and $R_2$, $R_3$, $R_5$ and $R_6$ are hydrogen, i.e. a compound of the formula

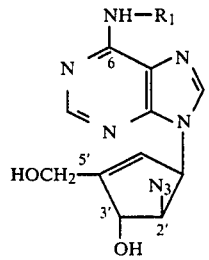

[A4]

wherein $R_1$ is hydrogen or benzoyl, is produced by reacting compound [4] with an alkali metal azide to obtain a compound of

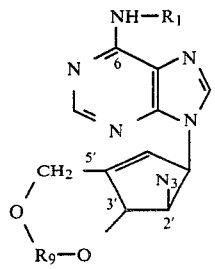

wherein R₉ is —Si(i—Pro)₂—O—Si(i—Pro)₂—, i—Pro is isopropyl and R₁ has the same meaning as hereinbefore, and removing the 3′,5′-O-protective group with tetrabutyl ammonium fluoride.

Examples of alkali metal azide are lithium azide, potassium azide and sodium azide. The preferred organic solvent in the azidation reaction is hexamethylphosphoramide. The azidation reaction proceeds at room temperature and hence it is not necessary to heat unless the reaction rate is too slow.

Removal of the 3′,5′-O-protective group from compound [8] can be performed by the same procwss as explained in (7) hereinbefore.

The thus-obtained compound can be purified as hereinafter explained.

(9) A compound [I], wherein R₁ is hydrogen or benzoyl, R₄ is amino, and R₂, R₃, R₅ and R₆ are hydrogen, i.e. a compound of the formula

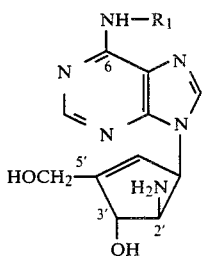

wherein R₁ is hydrogen or benzoyl, is produced by reducing compound [A4].

The reduction of the azide group to an amino group is performed by bubbling hydrogen sulfide in pyridine. The reaction proceeds at room temperature.

The thus-obtained compound [A5] can be purified as hereinafter explained.

(10) A compound [I], wherein R₁ is hydrogen or benzoyl, R₂ is hydrogen, and R₂, R₃, R₅ and R₆ are hydrogen, i.e. a compound of the formula

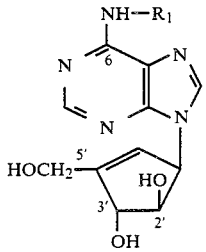

wherein R₁ is hydrogen or benzoyl, can be obtained by de-acetylation of compound [A1].

Deacetylation can be performed by treating with ammonia or an alkali metal alcoholate in methanol.

The 2′-acetoxy group together with the N⁶-benzoyl group are removed by treating with an alkali metal alcoholate such as sodium methylate.

The product [A6] can be purified by the method hereinafter explained.

(11) A compound [I], wherein R₁ is hydrogen or benzoyl, and R₂, R₃, R₄, R₅ and R₆ are hydrogen, i.e. a compound of the formula

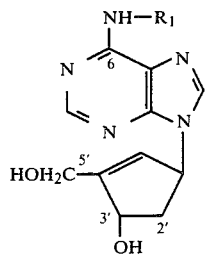

wherein R₁ is hydrogen or benzoyl, is produced by treating a compound [7] hereinbefore or a compound of the formula

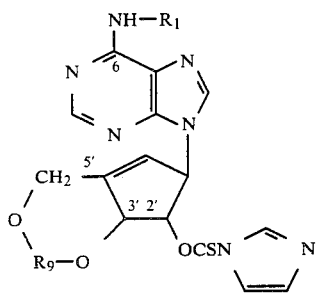

wherein R₁ is hydrogen or benzoyl, R₉ is OSi(i—Pro)₂—O—Si(i—Pro)₂— and i—Pro is isopropyl, with hydrogenated tin tributylate in an organic solvent to obtain a compound of the formula

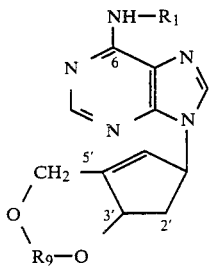

wherein R₁ and R₉ have the same meanings as hereinbefore, and removing the 3′,5′-O-protective group by treating with tetrabutyl ammonium fluoride.

The starting material [9] can be prepared by reacting compound [3] with N,N′-thiocarbonyldiimidazole in an organic solvent such as chloroform, methylene chloride or ethylene chloride. The reaction proceeds at room temperature. The reaction of the above compound [7] or [9] and hydrogenated tin tributylate is performed in an organic solvent such as benzene or toluene under heating. In the above reaction, azo bis-isobutylnitrile is preferably added as a catalyst and the reaction proceeds under an atmosphere of argon.

The 3',5'-O-protective group in the intermediate [10] obtained by the above reaction is removed by the same method as explained hereinbefore (1).

The thus-obtained compound [A7] can be purified by the method hereinbefore explained.

(12) A compound [I], wherein $R_1$ is hydrogen or benzoyl, $R_2$ and $R_3$ are hydrogen, $R_4$ is acetoxy or halogen, and $R_5$ and $R_6$ are acetyl, i.e. a compound of the formula

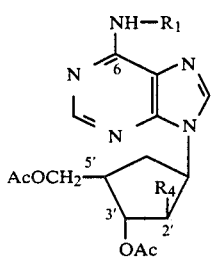
[A8]

wherein $R_1$ is hydrogen or benzoyl, and $R_4$ is acetoxy or halogen, is produced by acetylating compound [A1] or [A3].

The acetylation reaction is conducted by reacting with acetic anhydride in pyridine at room temperature. The resulting compound [A8] is purified by the method hereinbefore explained.

The compound [I] hereinabove and its intermediates can be isolated and purified by vacuum concentration, extraction, crystallization or chromatography using silica-gel, active carbon, cellulose or Sephadex.

In case compound [I] is a basic substance, for example compound [A5] can be isolated as an acid addition salt thereof. In that case, the base is neutralized with acid, and the acid addition salt thereof is crystallized or subjected to column chromatography to purify the product.

The growth-inhibitory activities of compound [I] of the present invention on L 5178 Y cells are shown below. (1) Test method:

A test sample (0.3 ml) dissolved in a medium [bovine serum (10%) in Fischer's medium] is added to a mouse lymphoma L 5178 Y cells suspension (2.7 ml, $5 \times 10^4$/ml cells), and the mixture is incubated at 37° C. for 22 hours. Cell-growth is observed by checking the color change of phenol red in the medium. The minimum inhibitory concentration (MIC) of the substance on cell growth is defined by observing apparent growth inhibition as compared with that of control.

(2) Test results:

| | MIC (γ/ml) |
|---|---|
| 2',3',5'-O—triacetyl nephlanocin A | 0.8 |
| 2',3'-O—benzylidene neplanocin A | 4 |
| $N^6,N^6,5'$-O—tribenzoyl neplanocin A | 0.16 |
| $N^6,5'$-O—dibenzoyl neplanocin A | 0.16 |

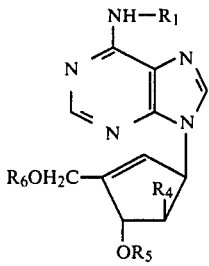

| $R_1$ | $R_4$ | $R_5$ | $R_6$ | γ/ml |
|---|---|---|---|---|
| H | H | H | H | 4 |
| H | Cl | H | H | 20 |
| H | Br | H | H | 4 |
| H | I | H | H | 4 |
| H | $N_3$ | H | H | 100 |
| H | $NH_2$ | H | H | 4 |
| H | Cl | Ac | Ac | 100 |
| COPh | I | H | H | 100 |

The following examples illustrate the process of manufacture of compound [I] of the present invention. In these examples, the carriers and developers on thin layer chromatography (TLC) are, if not specified, as follows:

Carrier: silica-gel (Merck, Art. 5729)
Developer:
 1. Chloroform-methanol (1:1)
 2. Chloroform-methanol (5:1)
 3. Chloroform-methanol (10:1)
 4. Chloroform-methanol (20:1)
 5. Chloroform-methanol (40:1)
 6. Benzene-ethyl acetate (1:1)
 7. Chloroform-ethanol (10:1)
Carrier: silica-gel (merck, Art. 5715)
Developer:
 8. Propyl alcohol-water-conc. aqueous ammonia (6:3:1)
 9. Acetone-water (10:3)

EXAMPLE 1

2',3',5'-O-triacetyl neplanocin A

Acetic anhydride (0.28 ml) was added dropwise to neplanocin A (263 mg) suspended in pyridine (5 ml) while stirring at room temperature. After reaction for 2.5 hours at room temperature, the reaction mixture was concentrated in vacuo below 40° C. The residue was extracted three times with chloroform then washed with water. The chloroform layer was passed through Whatman 1PS filter paper and concentrated in vacuo. The residue was charged on a column of silica gel (6 g) and eluted with chloroform-ethanol (30:1). Fractions showing $Rf_7 = 0.45$ by TLC were collected and concentrated in vacuo to obtain as a hygroscopic powder 2',3',5'-O-triacetyl neplanocin A (174 mg).

Elementary analysis [$C_{17}H_{19}O_6N_5 \cdot \frac{1}{2}H_2O$]

| | C % | H % | N % |
|---|---|---|---|
| Found: | 51.63 | 4.95 | 17.54 |
| Calculated: | 51.64 | 5.01 | 17.71 |

UV: λmax (methanol)=262 nm
Mass: 389 (M+), 346, 330, 329, 288, 287, 244, 228, 227, 136, 137.

NMR: δppm (CDCl$_3$) 2.01 (3H, S.OCOCH$_3$), 2.10 (6H, S.OCOCH$_b$3×2), 4.75 (2H, J≃0, H-5'), 5.57 (1H, d.c., H-2'), 5.82 (3H, broad, NH$_2$ and H-3'), 5.99 (1H, d., H-1'), 6.11 (1H, J≃0, H-6'), 7.80 (1H, S., H-2), 8.33 (1H, S., H-8).

EXAMPLE 2

2',3'-O-benzylidene neplanocin A

A mixture of neplanocin A (263 mg, 1 mM), zinc chloride (340 mg) and benzaldehyde (2 ml) is stirred at room temperature for 1.5 days. Diethyl ether is added to the reaction mixture, and the precipitate is filtered and washed with diethyl ether. The precipitate dissolved in ethyl acetate was washed three times with water. The ethyl acetate layer was passed through Whatman 1 PS filter paper and concentrated in vacuo. The residue was recrystallized from ethyl acetate to obtain 2',3'-O-benzylidene neplanocin A (301 mg).

m.p.: 226°–229° C.
TLC: Rf$_2$=0.62
Mass: 351 (M+), 245, 216, 136, 135.
NMR: δppm (DMSO-d$_6$) 4.19 (2H, slightly broad, H-5'), 4.85 (1H, d., H-2'), 5.10 (1H, t., OH-5', exchanged by D$_2$O, 5.41 (1H, d., H-3'), 5.58 (1H, broad, H-1'), 5.75 (1H, S., H-6'), 5.90 (1H, S., >CH-Ph), 7.24 (2H, broad, NH$_2$, exchanged by D$_2$O), 7.41 (5H, S., phenyl proton), 8.00 (1H, S., H-2), 8.12 (1H, S., H-8).

EXAMPLE 3

2',3'-O-isopropylidene neplanocin A

70% perchloric acid (0.9 ml) was added to neplanocin A (1.0 g) suspended in dry acetone (100 ml), and the mixture was stirred at room temperature for 2 hours, then the reaction mixture was homogenized. The reaction mixture was adjusted to pH 8-9 by adding aqueous ammonia. The precipitated crystals were cooled, filtered, washed with acetone and dried to obtain 2',3'-O-isopropylidene neplanocin A (682 mg).

m.p.: 256°–259° C.
Elementary analysis [C$_{14}$H$_{17}$O$_3$N$_5$]:

|  | C % | H % | N % |
|---|---|---|---|
| Found: | 55.39 | 5.77 | 22.89 |
| Calculated: | 55.43 | 5.65 | 23.09 |

NMR: δppm (DMSO-d$_6$) 1.28, 1.39 (each 3H, each S., CH$_3$×2), 4.15 (2H, slightly broad, H-5'), 4.68 (1H, d., H-2'), 5.07 (1H, 5., OH-5'), 5.33 (1H, d., H-3'), 5.45 (1H, J≃0, H-1'), 5.71 (1H, J≃0, H-6'), 7.25 (2H, slightly broad, NH$_2$), 7.96 (1H, S., H-2), 8.15 (1H, S., H-8).

EXAMPLE 4

N$^6$, N$^6$,5'-O-tribenzoyl-2',3'-O-isopropylidene neplanocin A.

2',3'-O-isopropylidene neplanocin A (303 mg) was dissolved in pyridine (10 ml). Benzoyl chloride (0.47 ml) was added dropwise while stirring at room temperature, then the mixture was stirred for 20 hours at room temperature. Water was added to the reaction mixture, which was then concentrated in vacuo and the residue extracted with chloroform. The chloroform layer was washed with saturated sodium bicarbonate solution and water, passed through Whatman 1PS filter paper, and concentrated in vacuo. The residue was charged on a column of silica gel (10 g) and eluted with chloroform. Fractions showing Rf$_5$=0.55 by TLC were collected and concentrated in vacuo to obtain N$^6$,N$^6$,5'-O-tribenzoyl-2',3'-O-isopropylidene neplanocin A (510 mg, yield: 83%).

TLC: Rf$_5$=0.55
Mass: 615 (M$^{30}$), 600, 587, 510, 482, 344, 343, 342, 240, 239, 238, 215, 105.
NMR: δppm (CDCl$_3$) 1.49, 1.52 (each 3H, each S, isopropylidene), 4.81 (1H, d., H-2'), 5.12 (2H, slightly broad, H-5'), 5.50 (1H, d., H-3'), 5.68 (1H, slightly broad, H-1'), 5.89 (1H, slightly broad, H-6'), 7.2~8.2 (16H, phenyl proton and H-2 or H-8).

EXAMPLE 5

N$^6$,5'-O-dibenzoyl neplanocin A

N$^6$,N$^6$,5'-O-tribenzoyl-2',3'-O-isopropylidene neplanocin A (62 mg) was suspended in 60% aqueous formic acid (2 ml) and methanol (0.5 ml) was added thereto, then the mixture was stirred at room temperature for one day and at 60° C. for 5 hours. The reaction mixture was concentrated in vacuo. Methanol was added to the residue and the mixture was again concentrated in vacuo. This operation was repeated until formic acid could ot be detected. The thus-obtained crystals were recrystallized twice from methanol to obtain N$^6$,5'-O-dibenzoyl neplanocin A.

m.p.: 202°–205° C.
Elementary analysis [C$_{25}$H$_{21}$O$_5$N$_5$]:

|  | C % | H % | N % |
|---|---|---|---|
| Found: | 63.70 | 4.55 | 14.76 |
| Calculated: | 63.68 | 4.49 | 14.86 |

Mass: 471 (M+), 366, 239.
NMR: δppm (DMSO-d$_6$) 4.48 (1H, m., H-2', d. by D$_2$O, d.), 4.64 (1H, m., H-3', d. by D$_2$O), 5.02 (2H, slightly broad H-5'), 5.25 (1H, d., OH, exchanged by D$_2$O), 5.34 (1H d., OH, exchanged by D$_2$O), 5.58 (1H, m., H-1'), 6.05 (1H, J≃0, H-1'), 7.4~8.1 (10H, phenyl proton), 8.45 (1H, S., H-8 or H-2) 11.13 (1H, broad, NH, exchanged by D$_2$O).

EXAMPLE 6

N$^6$,N$^6$5'-O-tribenzoyl neplanocin A

In Example 5, the mother liquor in the recrystallization operation was treated with silica gel (merck, Art. 7747) thin layer chromatography to separate and purify N$^6$, N$^6$,5'-O-tribenzoyl neplanocin A.

NMR: δppm (CDCl$_3$) 4.44 (1H, dd., H-2'), 4.84 (1H, d., H-3'), 5.11 (2H, slightly broad, H-5'), 5.56 (1H, slightly broad, H-1'), 6.13 (1H, J≃0, H-6'), 7.2–8.2 (16H, phenyl proton and H-2 or H-8), 8.61 (1H, S., H-8 or H-2), OH group is distributed over a broad range and disappeared upon addition of D$_2$O.
Mass: 575, 470.

EXAMPLE 7

N$^6$,5'-O-dibenzoyl-2',3'-O-isopropylidene neplanocin A

N-bromosuccinimide (20 mg) and barium carbonate (10 mg) were added to N$^6$,N$^6$,5'-O-tribenzoyl-2',3'-O-isopropylidene neplanocin A (61.5 mg) dissolved in a mixture of dichloroethane (2 ml) and carbon tetrachloride (5 ml), and the mixture was stirred at 90° C. for 15 hours. Water was added to the reaction mixture, which was then stirred, and the organic layer was concentrated in vacuo. The residue was charged on a column of silica gel (3 g) and eluted with chloroform-methanol (40:1). Fractions showing Rf$_5$=0.30 were collected and concentrated in vacuo to obtain a powder of N$^5$,5'-O-dibenzoyl-2',3'-O-isopropylidene neplanocin A (41 mg).

NMR: δppm (CDCL$_3$) 1.40, 1.52 (each 3H, each S., CH$_3$×2), 4.80 (1H, d., H-2'), 5.12 (2H, slightly broad, H-5'), 5.52 (1H, d., H-3'), 5.71 (1H, slightly broad, H-1'), 5.90 (1H, slightly broad, H-6'), 7.3–8.2 (11H, phenyl proton, H-2 or H-8).

EXAMPLE 8

N$^6$,5'-O-dibenzoyl neplanocin A

A mixture of N$^6$,5'-O-dibenzoyl-2',3'-O-isopropylidene neplanocin A (51 mg), 60% formic acid (2 ml) and methanol (0.5 ml) was stirred at 60° C. for 5 hours. The reaction mixture was concentrated in vacuo and the residue was recrystallized from methanol to obtain N$^6$,5'-O-dibenzoyl neplanocin A (41 mg).

The analytical results were identical with N$^6$,5'-O-dibenzoyl neplanocin A obtained in Example 5.

EXAMPLE 9

2',3'-O-ethoxymethylene neplanocin A

Dimethylformamide (5 ml) and ethyl ortho formate (0.33 ml) were added to neplanocin A (263 mg). A dimethylformamide solution (13.5% W/V, 0.3 ml) of hydrogen chloride was added thereto and the homogenate was stirred at room temperature for 12 hours. Triethylamine (0.25 ml) was added to the reaction mixture with ice cooling. Precipitated triethylamine hydrochloride was filtered off and the filtrate was concentrated in vacuo. A small amount of water and triethylamine were added to the residue and completely neutralized. The precipitated crystals were filtered to obtain 2',3'-O-ethoxymethylene neplanocin A (275 mg, yield: 86.2%). Purification was performed by silica gel column chromatography using chloroform-methanol (1:1) as a developer. Fractions showing Rf$_2$=0.45 were collected and concentrated in vacuo to obtain the purified material.

m.p.: 196°–201° C.
TLC: Rf$_2$=0.45
Elementary analysis [C$_{14}$H$_{17}$N$_5$O$_4$·½H$_2$O]:

|  | C % | H % | N % |
|---|---|---|---|
| Found: | 51.71 | 5.38 | 21.52 |
| Calculated: | 51.21 | 5.52 | 21.33 |

Mass: 319 (M+), 274, 245, 135, 134.
NMR: δppm (CDCl$_3$) 1.10, 1.12 (total 3H, each t., —CH$_2$CH$_3$), 352 (2H, q., —OCH$_2$CH$_3$), 4.16 (2H, J≈O, H-5'), 4.80 (1H, d., H-2'), 5.08 (1H, broad, S., OH-5'), 5.48 (1H, S., =CH—OC $_2$H$_5$), 5.36, 5.66 (total 1H, each d., H-3'), 5.76 (1H, J≈O, H-1'), 5.94, 5.98 (total 1H, each S., H-6'), 7.27 (2H, broad, S., NH$_2$), 7.98 (1H, S., H-2 or H-8), 8.14 (1H., S., H-2 or H-8).

EXAMPLE 10

N$^6$,N$^6$,5'-O-tribenzoyl-2',3'-O-ethoxymethylene neplanocin A

A methylene chloride solution (5 ml) of benzoyl chloride (0.47 ml) was added dropwise to 2',3'-O-ethoxymethylene neplanocin A (319 mg) dissolved in pyridine (5 ml) while stirring. The reaction mixture was stirred with ice cooling overnight and at room temperature for 10 hours, then poured into ice water and stirred with chloroform. The chloroform layer was passed through Whatman 1PS filter paper, concentrated in vacuo and the residue was charged on a column of silica gel (6 g), and eluted with benzene-ethyl acetate (8:1). Fractions showing Rf$_4$=0.85 were collected and concentrated in vacuo to obtain N$^6$N$^6$,5'-O-tribenzoyl-2',3'-O-ethoxymethylene neplanocin A (431 mg).

TLC: Rf$_4$=0.85
UV: λ$_{max}$$^{MeOH}$=255 nm (sh.), 275 nm
Mass: 631 (M+), 603, 586, 498.
NMR: δppm (CDCl$_3$) 1.21 (3H, t., —CH$_2$CH$_3$), 3.62 (2H, q., —O—CH$_2$—CH$_3$), 4.92 (1H, d., H-2'), 5.12 (2H, broad S., H-5'), 5.66 (total 1H, each d., H-3'), 5.90 (1H, broad S., H-1'), 5.97, 6.00 (total 1H, each S., H-6'), 7.2–8.1 (16H, m., phenyl proton and H-2 or H-8), 8.58, 8.59 (total 1H, each S., H-8 or H-2)

EXAMPLE 11

N$^6$,5'-O-dibenzoyl neplanocin A

60% formic acid (1 ml) and methanol (0.5 ml) were added to N$^6$, N$^6$5'-O-tribenzoyl-2',3'-O-ethoxymethylene neplanocin A (78 ml) and the mixture was stirred at room temperature for 30 minutes. N$^6$,5'-O-dibenzoyl neplanocin A and N$^6$,N$^6$,5'-O-tribenzoyl neplanocin A were detected by TLC (developer No. 4). The reaction mixture was concentrated in vacuo. The residue was dissolved in ethanol, adjusted to pH 8 with aqueous ammonia and allowed to stand at room temperature. The precipitated crystals were filtered, washed with ethanol and dried in vacuo to obtain N$^6$,5'-O-dibenzoyl neplanocin A (43 mg). The analytical results were identical with N$^6$,5'-O-dibenzoyl neplanocin A obtained in Example 5.

EXAMPLE 12

N$^6$-benzoyl neplanocin A (1) A methylene chloride solution (5 ml) of benzoyl chloride (0.78 ml) was added dropwise with stirring with ice cooling to neplanocin A (263 mg) dissolved in anhydrous pyridine (5 ml). The temperature was gradually increased to room temperature and the mixture was stirred for 8 hours. The reaction mixture was poured into ice water and extracted three times with chloroform. The combined extracts were washed with water, passed through Whatman 1PS filter paper and concentrated in vacuo. The residue was purified by silica gel column chromatography using chloroform to obtain a powder of N$^6$,N$^6$,2'-0,3'-0,5'-O-pentabenzoyl neplanocin A (587 mg).

NMR: δppm (CDCl$_3$) 5.16 (2H, J≈O, H-5'), 5.98 (1H, q., H-2'), 6.06 (1H, J≈O, H-1'), 6.31 (1H, J≈O, H-6'), 6.50 (1H, d., H-3'), 7.2–8.1 (25H, m., phenyl proton), 8.15 (1H, S., H-2), 8.56 (1H, S., H-8 ).

(2) The product (500 mg) obtained in the above (1) was dissolved in ethanol (3 ml) and pyridine (1.5 ml). A mixture of 2N-sodium hydroxide (3 ml) and ethanol (3 ml) was added at once and the mixture was stirred for 5 minutes. The reaction mixture was neutralized by adding Dowex 50 (pyridinium type), and the resulting material was filtered and washed with ethanol followed by pyridine. The filtrate and washings were collected, concentrated in vacuo and methanol was added thereto to obtain N$^6$-benzoyl neplanocin A crystals (187 mg).

m.p.: 180–183° C.
NMR: δppm (DMSO-d$_6$) 4.16 (2H, m., H-5'), 4.36 (1H, q., H-2'), 4.44 (1H, t., H-3'), 4.94 (1H, t., 5'-OH, exchanged by D$_2$O), 5.02 (1Hd, OH, exchanged by D$_2$O), 5.21 (1Hd, OH, exchanged by D$_2$O), 5.50 (1H, m., H-1'), 5.76 (1H, J≈O, H-6'), 7.4–8.1 (5H, m., phenyl proton), 8.40 (1H, S., H-2), 8.70 (1H, S., H-8), 10.38 (1H, S., NH, exchanged by D$_2$O)

EXAMPLE 13

3',5'-O-(1,1,3,3-tetraisopropyl disiloxane-1,3-di-yl) neplanocin A.

Neplanocin A (236 mg) and imidazole (300 mg) were dissolved in dimethylformamide (3 ml). 1,3-dichloro-1,1,3,3-tetraisopropyl disiloxane (350 mg) was added thereto and the mixture was stirred at room temperature for 40 minutes. Water (20 ml) was added to the reaction mixture which was then ice cooled to precipitate the oily material which was decanted and dissolved in chloroform, then washed with water. The organic layer was passed through Whatman 1PS filter paper and concentrated in vacuo. The residue was purified by silica gel column chromatography using chloroform-ethanol (30:1). Fractions showing Rf$_3$=0.50 were collected and dried in vacuo to obtain 3',5'-O-(1,1,3,3-tetraisopropyl disiloxane-1,3-di-yl) neplanocin A (212 mg).

m.p.: 185°–186° C.

Elementary analysis [C$_{23}$H$_{39}$O$_4$N$_5$Si$_2$]:

|  | C % | H % | N % |
|---|---|---|---|
| Found: | 54.47 | 7.79 | 13.81 |
| Calculated: | 54.62 | 7.77 | 13.85 |

NMR: δppm (CDCl$_3$) 1.1 (28H, isopropyl), 3.59 (1H, d., OH-2', exchanged by D$_2$O), 4.32 (1H, Sextet, H-2', d.d by D$_2$O), 4.52 (2H, slightly broad, H-5'), 5.32 (1H, d., H-3'), 5.50 (1H, slightly broad, H-1'), 5.60 (2H, slightly broad, NH -6, exchanged by D$_2$O), 5.83 (1H, H-6'), 7.76 (1H, S., H-2), 8.36 (1H, S., H-8).

Mass: 505 (M$^+$), 462 (M$^+$ −43), 136, 135.

EXAMPLE 14

N$^6$-benzoyl-3',5'-O-(1,1,3,3-tetraisopropyl disiloxane-1,3-di-yl) neplanocin A N$^6$-benzoyl neplanocin A (926 mg) and imidazole (755 mg) were dissolved in dry dimethylformamide (15 ml). 1,3-dichloro1,1,3,3-tetraisopropyl disiloxane (870 mg) was added thereto and the mixture was stirred at room temperature for 10 minutes. Water was added with ice cooling, and the mixture was concentrated in vacuo and the residue was extracted with chloroform. The organic layer was washed with water, passed through Whatman 1PS filter paper and concentrated in vacuo. The residue was purified by Florisil column chromatography using chloroform-methanol (30–20:1) (1.25 g, yield: 82%).

NMR: δppm (CDCl$_3$) 1.1 (28H, isopropyl), 3.48 (1H, d., OH-2', exchanged by D$_2$O), 4.34 (1H, Sextet, H-2', d.d. by D$_2$O), 4.50 (2H, slightly broad, H-5'), 5.34 (1H, d., H-3'), 5.55 (1H, slightly broad, H-1'), 5.82 (1H, h-6'), 7.4–8.1 (6H, phenyl proton and H-2 or H-8), 8.78 (1H, S., H-8 or H-2), 8.96 (1H, broad, NH, exchanged by D$_2$O).

UV: λ$_{max}^{MeOH}$=282 nm

Mass: 609 (M$^+$), 566 (M$^+$ −43)

EXAMPLE 15

2'-O-trifluoromethanesulfonyl-3',5'-O-(1,1,3,3-tetraisopropyl disiloxane-1,3-di-yl) neplanocin A.

4-dimethylaminopyridine (570 mg) and triethylamine (0.65 ml) were added to 3',5'-O-(1,1,3,3-tetraisopropyl disiloxane-1,3-di-yl) neplanocin A (2.36 g) dissolved in dry pyridine (15 ml). Trifluoromethanesulfonylchloride (0.5 ml) was added dropwise thereto while stirring with ice cooling. The temperature was gradually increased to room temperature. The reaction mixture was stirred for 30 minutes, poured into ice water, then extracted several times with chloroform. The extract was washed with water, passed through Whatman 1PS filter paper and concentrated in vacuo. The residue was purified by silica gel column chromatography using chloroform-ethanol (30:1). Fractions showing Rf$_3$=0.16 were collected and concentrated in vacuo to obtain porous 2'-O-trifluoromethanesulfonyl-3',5'-O-(1,1,3,3-tetraisopropyl disiloxane-1,3-di-yl) neplanocin A (2.1 g, yield: 70.5%).

NMR: δppm (CDCl$_3$) 1.1 (28H, isopropyl), 4.51 (2H, slightly broad, H-5'), 5.38 (1H, d.d., H-2'), 5.58 (3H, 6-NH$_2$ and H-3', d. by D$_2$O, h-3'), 5.69 (1H, m., H-1'), 5.94 (1H, J=O,H-6'), 7.73 (1H, S., H-2), 8.32 (1H, S., H-8)

UV: λ$_{max}^{MeOH}$=262 nm

Mass: 594 (M$^+$ −43), 495, 477, 367, 253, 235, 135.

EXAMPLE 16

N$^6$-benzoyl-2'-O-trifluoromethanesulfonyl-3',5'-O-(1,1,3,3-tetraisopropyl disiloxane-1,3-di-yl) neplanocin A Triethylamine (0.04 ml) and 4-dimethylaminopyridine (10 mg) were added to N$^6$-benzoyl-3',5'-O-(tetraisopropyl disiloxane-1,3-di-yl) neplanocin A (52 mg) dissolved in pyridine (1 ml). Trifluoromethanesulfonylchloride (0.01 ml) was added dropwise with ice cooling. The temperature was gradually increased to room temperature. The reaction mixture was stirred for 3 hours, poured into ice water and then extracted with chloroform. The organic layer was passed through Whatman 1PS filter paper and concentrated in vacuo. The residue was purified by silica gel column chromatography using chloroform-methanol (30:1) to obtain N$^6$-benzoyl-2'-O-trifluoromethanesulfonyl-3',5'-O-(1,1,3,3-tetraisopropyl disiloxane-1,3-di-yl) neplanocin A (48 mg).

NMR: δppm (CDCl$_3$) 1.1 (28H, isopropyl), 4.52 (1H, d.d., H-2'), 5.58 (1H, d., H-3'), 5.76 (1H, slightly broad, H-1'), 5.86 (1H, h-6'), 7.4–8.1 (6H, phenyl proton and H-2 or H-8), 8.75 (1H, S., H-8 or H-2), 9.00 (1H, broad, NH).

EXAMPLE 17

2'-(R)-acetoxy-2'-deoxy neplanocin A (1) Sodium acetate (163 mg) was added to 2'-O-trifluoromethanesulfonyl-3',5'-O-(1,1,3,3-tetraisopropyl disiloxane-1,3- di-yl) neplanocin A (1.06 g) dissolved in hexamethylphosphoramide (10 ml), and the mixture was stirred at room temperature for 1.5 days. The reaction mixture was poured into ice water, extracted with chloroform, the organic layer was washed with water, passed through Whatman 1PS filter paper and concentrated in vacuo. The residue was purified by silica gel column chromatography using chloroform-ethanol (30:1). Fractions showing Rf$_3$=0.36 were collected and dried in vacuo to obtain 2'-(R)-acetoxy-2'-deoxy-3',5'-

O-(1,1,3,3-tetraisopropyl disiloxane-1,3-di-yl) neplanocin A (270 mg).

NMR: δppm (CDCl₃) 1.1 (28 H, isopropyl), 1.61 (3H, S., OCOCH₃), 4.45 (2H, slightly broad, H-5'), 5.32 (1H, t., H-3'), 5.44 (1H d.d., H-2'), 5.6–6.0 (4H, NH₂ and H-6', H-1', 2H by D₂O), 7.69 (1H, S., H-2), 8.34 (1H, S., H-8).

UV: $\lambda_{max}^{MeOH}$=261 nm

Mass: 547 (M⁺), 504 (M+- 43), 352, 228, 136, 135.

(2) The product obtained in the above (1) (270 mg) was dissolved in anhydrous tetrahydrofuran (4 ml). Tetrabutylammonium fluoride (140 mg) was added thereto while stirring at room temperature. Immediately oily material was precipitated and stirring was continued for a further 10 minutes. The reaction mixture was concentrated in vacuo and the residue was recrystallized from ethanol to obtain 2'-(R)-acetoxy-2'-deoxy neplanocin A (120 mg, yield: 80%).

m.p.: 195°–197° C.

Elementary analysis [$C_{13}H_{15}O_4N_5$]:

|  | C % | H % | N % |
|---|---|---|---|
| Found: | 51.12 | 4.98 | 22.74 |
| Calculated: | 51.14 | 4.95 | 22.94 |

NMR: δppm (DMSO-d₆) 1.52 (3H, S., OCOCH₃), 4.17 (2H, slightly broad, H-5'), 4.82 (1H, slightly broad, H-3', d by D₂O), 4.97 (1H, t., OH-5', exchanged by D₂O), 5.18 (1H, d.d., H-2'), 5.55 (1H, d., OH-3', exchanged by D₂O), 5.64 (1H, d.d., H-1'), 5.80 (1H, d., H-6'), 7.18 (2H, broad, S., NH₂, exchanged by D₂O), 7.82 (1H, S., H-2), 8.11 (1H, S., H-8).

UV: $\lambda_{max}^{MeOH}$=262 nm

Mass: 306 (M⁺−1), 305 (M⁺), 304, 287, 262, 245, 136, 135

CD: [θ]−11,900 (252 nm, H₂O)

EXAMPLE 18

2'-(R)-hydroxy-2'-deoxy neplanocin A

Methanolic ammonia [ammonia-gas-saturated methanol (50 ml) at 0° C.] was added to 2'-(R)-acetoxy-2'-deoxy neplanocin A (74 mg) and the mixture was stirred at room temperature for 3.5 hours. The reaction mixture was dried in vacuo. The residue was recrystallized from aqueous ethanol to obtain 2'-(R)-hydroxy-2'-deoxy neplanocin A (185 mg, yield: 92%).

m.p.: 239°–240.5° C.

Elementary analysis [$C_{11}H_{13}O_3N_5 \cdot \frac{1}{3}H_2O$]:

|  | C % | H % | N % |
|---|---|---|---|
| Found: | 49.01 | 5.01 | 25.97 |
| Calculated: | 49.13 | 5.00 | 26.04 |

NMR: δppm (DMSO-d₆) 4.14 (3H, m., H-5' and H-2'), 4.56 (1H, t., H-3', d by D₂O), 4.86 (1H, t., OH-5', exchanged by D₂O), 5.18, 5.22 (each 1H, each d., OH-2' and OH-3', exchanged by D₂O), 5.52 (1H, d.d., H-1'), 5.72 (1H, J≃0, H-6'), 7.10 (2H, slightly broad, S., NH₂), 7.78 (1H, S., H-2), 8.12 (1H, S., H-8)

UV: $\lambda_{max}^{H_2O}$=262 nm

Mass: 264 (M⁺+1), 263 (M⁺), 245, 216, 186, 136, 135.

TLC: Rf₂=0.10, Rf=0.46 [ethanol+boric acid in aqueous ammonium acetate (0.5 M) (5:2), silica gel plate]

EXAMPLE 19

N⁶-benzoyl-2'-(R)-acetoxy-2'-deoxy neplanocin A.

N⁶-benzoyl-2'-trifluoromethanesulfonyl-3',5'-O-(1,1,3,3tetraisopropyl disiloxane-1,3-di-yl) neplanocin A (30 mg) was dissolved in hexamethylphosphoramide (0.5 ml). Sodium acetate (3.7 mg) was added thereto and the mixture was stirred at room temperature for 6.5 hours. Further sodium acetate (3 mg) was added thereto and the mixture was stirred for 12 hours. The reaction mixture was extracted with chloroform and washed with water. The organic layer was concentrated in vacuo, and purified by silica gel TLC using benzene-ethyl acetate (1:1). The band showing Rf₆=0.21 was collected, extracted with chloroform-methanol (1:1) and dried in vacuo to obtain N⁶-benzoyl-2'-(R)-acetoxy-2'-deoxy-3',5'-(1,1,3,3-tetraisopropyl disiloxane-1,3-di-yl) neplanocin A (10 mg).

NMR: δppm (DMSO-d₆) 1.1 (28H, isopropyl), 1.60 (3H, S., PCPCH3), 4.46 (2H, slightly broad, H-5'), 5.3–5.5 (2H, m., H-2' and H-3'), 5.87 (2H, H-6' and H-1'), 7.4–8.1 (6H, phenyl proton and H-2 or H-8), 8.76 (1H, S., H-8 or H-2), 9.04 (1H, broad, NH)

Mass: 651 (M⁺), 608, 622, 591, 504, 369, 352, 105.

(2) The product obtained in the above (1) (45 mg) was dissolved in anhydrous tetrahydrofuran (1 ml). Tetrabutylammonium (21 mg) was added thereto and the mixture was stirred at room temperature for 10 minutes. The reaction mixture was concentrated in vacuo and the residue was recrystallized from ethanol to obtain N⁶-benzoyl-2'-(R)-acetoxy-2'-deoxy neplanocin A (15 mg).

m.p.:205°–207° C.

NMR: δppm (DMSO-d₆) 1.52 (3H, S., OCOCH₃), 4.02 (2H, m., H-5'), 4.88 (1H, d.d., H-3', d. by D₂O), 5.03 (1H, t., OH-5'), exchanged by D₂O), 5.26 (1H, d.d., H-2'), 5.62 (1H, d., OH-3', exchanged by D₂O), 5.87 (2H, H-6' and H-1'), 7.4–8.1 (5H, m., phenyl proton), 8.22 (1H, S., H-2 or H-8), 8.71 (1H, S., H-8 or H-2), 11.13 (1H, broad, NH, exchanged by D₂O)

Mass: 409 (M⁺), 408, 349, 304, 228, 105.

UV: $\lambda_{max}^{MeOG}$=281 nm

Elementary analysis [$C_{20}H_{19}N_5O_5 \cdot \frac{1}{2}H_2O$]:

|  | C % | H % | N % |
|---|---|---|---|
| Found: | 57.55 | 4.78 | 16.70 |
| Calculated: | 57.41 | 4.82 | 16.74 |

EXAMPLE 20

2'-(R)-hydroxy-2'-deoxy neplanocin A

N⁶-benzoyl-2'-(R)-acetoxy-2'-deoxy neplanocin A (5 mg) was suspended in methanol (2 ml). The suspension was adjusted to pH 10 by adding a methanol solution of sodium methoxide. A homogeneous solution was obtained. After checking the disappearance of the starting material, the solution was neutralized by Dowex 50 (H⁺). The resin was washed with water, eluted with aqueous ammonia-methanol and concentrated in vacuo. The residue was charged on a TLC plate and eveloped by benzene-ethyl acetate (1:1). The band showing Rf₂=0.10 was collected, extracted with chloroform-methanol (1:1) and dried in vacuo to obtain 2'-(R)-hydroxy-2'-deoxy neplanocin A. The thus-obtained product was identical with the compound obtained in Example 18, according to instrumental analysis.

EXAMPLE 21

2'-(R)-azide-2'-deoxyneplanocin A (1) 2'-O-trifluoromethanesulfonyl-3',5'-O-(1,1,3,3-tetraisopropyl disiloxane-1,3-di-yl) neplanocin A (63.7 mg) obtained in Example 15 was dissolved in hexamethylphosphoramide (0.5 ml). Lithium azide (8.5 mg) was added thereto and the mixture was stirred at room temperature for 10 hours. The reaction mixture was extracted with chloroform, washed with water and concentrated in vacuo. The residue was charged on a silica gel TLC plate and developed by benzene-ethyl acetate (1:1). The band showing $Rf_6=0.10$ was collected, extracted with chloroform-methanol (1:1) and dried in vacuo. The product was recrystallized from methanol to obtain 2'-(R)-azide-2'-deoxy-3',5'-O-(1,1,3,3-tetraisopropyl disiloxane-1,3-di-yl) neplanocin A (43 mg, yield: 81%).

m.p.: 189°–191° C. (white needle crystals)

Elementary analysis [$C_{23}H_{38}O_3N_8Si_2$]:

|  | C % | H % | N % |
|---|---|---|---|
| Found: | 51.81 | 7.19 | 20.95 |
| Calculated: | 52.04 | 7.22 | 21.11 |

NMR: δppm (CDCl$_3$) 1.1 (28H, isopropyl), 4.27 (1H, d.d., H-2'), 4.44 (2H, S., H-5), 5.06 (1H, d., H-1'), 5.84 (1H, J≃O, H-6'), 7.64 (1H, S., H-2), 8.38 (1H, S., H-8).

UV: $\lambda_{max}^{MeOH}=262$ nm

Mass: 530 (M$^+$), 488 (M$^+$ 42), 487 (M$^+$ −43), 432, 324.

IR: $\nu N_3$ (KBr) 2110 cm$^{-1}$.

(2) 2'-(R)-azide-2'-deoxy-3',5'-O-(1,1,3,3-tetraisopropyl disiloxane-1,3-di-yl) neplanocin A (250 mg) obtained in the above (1) was dissolved in anhydrous tetrahydrofuran (5 ml). Tetrabutylammonium fluoride (135 mg) was added dropwise with stirring at room temperature for 5 minutes. The reaction mixture was concentrated in vacuo. The residue was recrystallized from ethanol to obtain 2'-(R)-azide-2'-deoxy neplanocin A (11g mg, yield: 82%).

m.p.: 231–233° C. (decomp.)

Elementary analysis [$C_{11}H_{12}O_2N_8$]:

|  | C % | H % | N % |
|---|---|---|---|
| Found: | 45.86 | 4.25 | 38.66 |
| Calculated: | 45.83 | 4.20 | 38.77 |

NMR: δppm (DMSO-d$_6$) 4.15 (2H, slightly broad, H-5'), 4.27 (1H, d.d., H-2'), 4.81 (1H, t., H-3'), 4.95 (1H, t., OH-5', exchanged by D$_2$O), 5.64 (1H, d.d., H-1'), 5.75 (1H, d., OH-3', exchanged by D$_2$O), 5.77 (1H, J≃O, H-6'), 7.21 (2H, broad, S., NH2, exchanged by D$_2$O), 7.88 (1H, S., H-2), 8.15 (1H, S., H-8).

UV: $\lambda_{max}^{H_2O}=262$ nm.

Mass: 289 (M$^+$ +1), 288 (M$^+$), 246 (M$^+$-42), 186, 136, 135.

IR: $\nu N_3$ (KBr) 2115 cm$^{-1}$

CD: [θ]−19,900 (253 nm, H$_2$O)

EXAMPLE 22

2'-(R)-chloro-2'-deoxy neplanocin A

2'-O-trifluoromethanesulfonyl-3',5'-O-(1,1,3,3-tetraisopropyl disiloxane-1,3-di-yl) neplanocin A (500 mg) obtained in Example 15 was dissolved in hexamethylphosphoramide (5 ml). Lithium chloride (43 mg) was added thereto and the mixture was stirred at room temperature for 20 hours. The reaction mixture was poured into ice water and extracted with chloroform. The organic layer was washed with water, passed through Whatman 1PS filter paper, then concentrated in vacuo. The residue was charged on a silica gel TLC plate and developed by chloroform-ethanol (15:1). The band showing $Rf_3=0.51$ was collected, extracted with chloroform-methanol (1:1) and dried in vacuo to obtain 2'-(R)-chloro-2'-deoxy-3',5'-O-(1,1,3,3-tetraisopropyl disiloxane-1,3-di-yl) neplanocin A. The product was dissolved in anhydrous tetrahydrofuran, and tetrabutylammonium fluoride was added thereto while stirring at room temperature to remove the protective silyl group. The reaction mixture was concentrated in vacuo. The residue was charged on a silica gel TLC plate, and developed by chloroform-methanol (5:1). The band showing $Rf_2=0.14$ was collected, extracted with chloroform-methanol (1:1) and concentrated in vacuo. The residue was recrystallized to obtain 2'-(R)-chloro-2'-deoxy neplanocin A (120 mg, yield: 55%).

m.p.: 233°–235° C. (decomp.)

Elementary analysis [$C_{11}H_{12}O_2N_5Cl$]:

|  | C % | H % | N % | Cl % |
|---|---|---|---|---|
| Found: | 46.88 | 4.32 | 24.79 | 12.51 |
| Calculated: | 46.90 | 4.29 | 24.86 | 12.59 |

NMR: δppm (DMSO-d$_6$) 4.16 (2H, slightly broad, H-5'), 4.54 (1H, d.d., H-2'), 4.91 (1H, t., H-3'), 5.00 (1H, t., OH-5', exchanged by D$_2$O), 5.74 (1H, d.d., H-1'), 5.85 (1H, d., OH-3', exchanged by D$_2$O), 5.86 (1H, J OH-6'), 7.21 (2H, broad, S., NH2, exchanged by D$_2$O), 7.96 (1H, S., H-2), 8.14 (1H, S., H-8).

UV: $\lambda_{max}^{H_2O}=262$ nm

Mass: 284, 282 (M$^+$ +1), 283, 281 (M$^+$), 136, 135.

CD: [θ] −10,800 (252 nm. H$_2$O)

EXAMPLE 23

2'-(R)-chloro-2'-deoxy-3'-O,5'-O-diacetyl neplanocin A.

Acetic anhydride (0.02 ml) was added to 2'-(R)-chloro-2'-deoxy neplanocin A (30 mg) dissolved in anhydrous pyridine (1 ml) and the mixture was stirred at room temperature for 8 hours. The reaction mixture was concentrated in vacuo. The residue was recrystallized from ethanol to obtain 2'-(R)-chloro-2'-deoxy-3'-0,5'-O-diacetyl neplanocin A (32 mg, yield: 82%).

m.p.: 179°–181° C.

TLC: $Rf_2=0.64$

NMR: δppm (CDCl$_3$) 2.14, 2.18 (each 3H, each S., OCOCH$_3$X3) 4.72 (1H, d.d., H-2'), 4.78 (2H, S., H-5), 5.68 (2H, broad, S., NH2, exchanged by D$_2$O), 6.0–6.1 (2H, H-1' and H-3'), 6.13 (1H, J ), H-6'), 7.78 (1H, S., H-2), 8.37 (1H, S., H-8)

UV: $\lambda_{max}^{MeOH}=262$ nm

Mass: 368, 366 (M$^+$ +1), 367, 365 (M$^+$), 330, 288, 136, 135.

EXAMPLE 24

2'-(R)-bromo-2'-deoxy neplanocin A

2'-trifluoromethanesulfonyl-3',5'-O-(1,1,3,3-tetraisopropyl disiloxane-1,3-di-yl) neplanocin A (500 mg) was dissolved in hexamethylphosphoramide (5 ml). Lithium bromide (70 mg) (anhydride obtained by heating the commercially available hydrated product) was added thereto and the mixture was stirred at room temperature for 2.5 hours. The reaction mixture was poured into ice water. The precipitated crystals were filtered, washed with water and dried in vacuo. Recrystallization was effected from cyclohexane to obtain 2'-(R)-bromo-2'-deoxy-3',5'-O-(1,1,3,3-tetraisopropyl disiloxane-1,3-di-yl) neplanocin A (440 mg).

m.p.: 175°–178° C.

Elementary analysis [$C_{23}H_{38}O_3N_5Si_2Br$]:

|  | C % | H % | N % | Br % |
|---|---|---|---|---|
| Found: | 48.56 | 6.77 | 12.27 | 14.13 |
| Calculated: | 48.58 | 6.74 | 12.32 | 14.05 |

NMR: δppm (CDCl$_3$) 1.1 (28H, isopropyl), 4.46 (2H, S., H-5'), 4.59 (1H, d.d., H-2'), 5.34 (1H, d., H-3'), 5.56 (2H, broad, S., NH$_2$, exchanged by D$_2$O), 5.78 (1H, d.d., H-1'), 5.90 (1H, J OH-6'), 7.69 (1H, S., H-2), 8.38 (1H, S., H-8).

UV: $\lambda_{max}^{MeOH} = 262$ nm

Mass: 569, 567 (M+), 526, 524, 488, 444, 353, 311.

CD: [θ] −15,300 (252 nm, MeOH)

(2) The product (200 mg) obtained in the above (1) was dissolved in anhydrous tetrahydrofuran (5 ml). Tetra-n-butylammonium fluoride (100 mg) was added thereto while stirring at room temperature for 5 minutes. The reaction mixture was concentrated in vacuo. The residue was charged on a TLC plate and developed by chloroform-methanol (5:1). The band showing Rf$_2$=0.30 was collected, extracted with chloroform-methanol (1:1), dried in vacuo, then recrystallized from ethanol. (95 mg, yield: 83%).

m.p.: 224°–226° C. (decomp.)

Elementary analysis [$C_{11}H_{12}O_2N_5br$]:

|  | C % | H % | N % | Br % |
|---|---|---|---|---|
| Found: | 40.57 | 3.63 | 21.26 | 24.24 |
| Calculated: | 40.50 | 3.71 | 21.47 | 24.50 |

NMR: δppm (DMSO-d$_6$) 4.17 (2H, slightly broad, H-5'), 4.60 (1H, d.d., H-2'), 4.93–5.06 (2H, H-3' and OH-5', 1H by D$_2$O), 5.70 (1H, d.d., H-1'), 5.84 (1H, d., OH-3'), exchanged by D$_2$O), 5.86 (1H, J≈O, H-6'), 7.20 (2H, broad, NH$_2$, exchanged by D$_2$O), 7.96 (1H, S., H-2), 8.14 (1H, S., H-8).

UV: $\lambda_{max}^{H2O} = 262$ nm

Mass: 327, 325 (M+), 246, 228, 136, 135.

CD: [θ] −13,000 (252 nm H$_2$O)

EXAMPLE 25

2'-(R)-iodo-2'-deoxy neplanocin A

In Example 24, lithium bromide was replaced by sodium iodide to obtain 2'-(R)-iodo-deoxy neplanocin A. Yield: 380 mg.

m.p.: 212°–215° C. (decomp.)

UV: $\mu_{max}^{H2O} = 262$ nm

EXAMPLES 26

N$^6$-benzoyl-2'-(R)-iodo-2'-deoxy neplanocin A.

(1) The compound (50 mg) obtained in Example 16 and lithium iodide (15 mg) were dissolved in hexamethylphosphoramide (1 ml) and the mixture was stirred at room temperature for 24 hours. The reaction mixture was dissolved in chloroform, washed with water, passed through Whatman 1PS filter paper and concentrated in vacuo. The residue was treated by TLC in the same way as in Example 25 to obtain N$_6$-benzoyl-2'-(R)-iodo-2'- deoxy-3',5'-O-(tetraisopropyl disiloxane-1,3-di-yl) neplanocin A (35 mg).

NMR: δppm (CDCl$_3$) 1.1 (28 H, isopropyl), 4.51 (2H, slightly broad, H-5'), 4.70 (1H, d.d., H-2'), 5.46 (1H, d., H-3'), 5.78 (1H, d.d., H-1'), 5.92 (1H, J≈O, H-6'), 7.4–8.1 (5H, m., phenyl proton), 7.88 (1H, S., H-2 or H-8), 8.83 (1H, S., H-8 or H-2), 8.98 (1H, broad, NH, exchanged by D$_2$O).

Mass: 676 (M+ −43), 477, 253, 240, 239, 238.

(2) The protective groups of the product obtained in the above (1) were removed by the same procedure as in Example 19-2) to obtain N$^6$-benzoyl-2'-(R)-iodo-2'-deoxy neplanocin A.

NMR: δppm (DMSO-d$_6$) 4.21 (2H, slightly broad, H-5'), 4.66 (1H, d.d., H-2'), 5.02 (1H, t., OH-5'), exchanged by D$_2$O), 5.13 (1H, t., H-3'), 5.78 (1H, d.d, H-1'), 5.84 (1H, d., OH-3', exchanged by D$_2$O), 5.90 (1H, J≈O, H-6'), 7.5–8.1 (5H, m., phenyl proton), 8.32 (1H, S., H-2), 8.75 (1H, S., H-8), 11.14 (1H, broad, NH, exchanged by D$_2$O).

EXAMPLE 27

2'-deoxy neplanocin A (1) 2'-(R)-bromo-2'-deoxy-3',5'-O-(1,1,3,3-tetraisopropyl disiloxane-1,3-di-yl) neplanocin A (500 mg), tin tri-n-butyl hydride (0.35 ml) and a catalytic amount of azobisisobutyronitrile were dissolved in benzene (5 ml), and refluxed under an argon stream for 3 hours. The reaction mixture was concentrated in vacuo. The residue was purified by silica gel column chromatography using chloroform-ethanol (40:1). Fractions showing Rf$_3$=0.24 were collected and concentrated in vacuo. The residue was recrystallized from ethanol to obtain 2'-deoxy-3',5'-O-(1,1,3,3tetraisopropyl disiloxane-1,3-di-yl) neplanocin A (385 mg, yield: 90%).

m.p.: 149°–151° C.

NMR: δppm (CDCl$_3$) 1.1 (28H, isopropyl), 2.3–2.6 (2H, 16 tet, H-2'), 4.49 (2H, S., H-5'), 5.39 (1H, d.d, H-3'), 5.72 (2H, S., NH2, exchanged by D$_2$O), 5.81 (2H, H-1' and H-6'), 7.75 (1H, S., H-2), 8.36 (1H, S., H-8).

UV: $\lambda_{max}^{MeOH} = 262$ nm

Mass: 489 (M+), 446, 354, 311, 212, 136, 135.

Elementary analysis [$C_{23}H_{39}O_3N_5Si_2\cdot\frac{1}{2}H_2O$]:

|  | C % | H % | N % |
|---|---|---|---|
| Found: | 55.75 | 7.87 | 14.09 |
| Calculated: | 55.38 | 8.08 | 14.04 |

(2) The compound (278 mg) obtained in the above (1) and tetrabutylammonium fluoride (200 mg) were dissolved in anhydrous tetrahydrofuran (3 ml) and the mixture was stirred at room temperature for 10 minutes. The reaction mixture was concentrated in vacuo. The residue was recrystallized from ethanol to obtain 2'-deoxy neplanocin A (115 mg, yield: 82%).

m.p.: 231°–234° C.

Elementary analysis [$C_{11}H_{13}O_2N_5$]:

|  | C % | H % | N % |
|---|---|---|---|
| Found: | 53.43 | 5.25 | 28.04 |

|  | C % | H % | N % |
|---|---|---|---|
| Calculated: | 53.43 | 5.30 | 28.33 |

TLC: $Rf_2 = 0.17$

NMR: δppm (DMSO-$d_6$) 2.2–2.4 (2H, m., H-2'), 4.15 (2H, slightly broad, H-5'), 4.8–5.0 (2H, t., +d.d., OH-5' and H-3'), 5.06 (1H, d., OH-3'), 5.64 (1H, m., H-1'), 5.75 (1H, J=0, H-6'), 7.17 (2H, slightly broad, NH$_2$), 7.97 (1H, S., H-2), 8.13 (1H, S., H-8).

UV: $\lambda_{max}^{H2O} = 262$ nm

Mass: 247 (M+), 229, 200, 186, 136, 135.

CD: [θ] −6,900 (252 nm, H$_2$O)

EXAMPLE 28

2'-(R)-amino-2'-deoxy neplanocin A acetate

2'-(R)-azide-2'-deoxy neplanocin A (80 mg) was dissolved in aqueous pyridine (50%, 5 ml). Hydrogen sulfide was bubbled therethrough at room temperature. The starting material disappeared wherein 6 hours and the reaction mixture was neutralized with 2 N-acetic acid, then concentrated in vacuo. Vacuum concentration was repeated twice by adding ethanol. Water was added to the residue and the insoluble material was removed. The supernatant solution was dried in vacuo. The residue was recrystallized from ethanol to obtain 2'-(R)-amino-2'-deoxy neplanocin A acetate (56 mg, yield: 72%).

TLC: $Rf_1 = 0.15$, $Rf_2 = 0$

NMR: δppm (DMSO-$d_6$) 2.50 (3H, S., CHCOO−), 3.29 (3H, broad, NH$_3$), 3.47 (1H, d.d., H-2'), 4.14 (2H, S., H-5'), 4.49 (1H, d., H-3'), 4.85 (1H, broad, OH-3' or OH-5'), 5.22 (1H, broad, OH-5' or OH-3'), 5.46 (1H, d., H-1'), 5.71 (1H, J≃O, H-6'), 7.17 (2H, slightly broad, NH$_2$), 7.84 (1H, S., H-2), 8.12 (1H, S., H-8).

UV: $\lambda_{max}^{H2O} = 262$ nm

Mass: 262 (M+), 244, 216, 186, 136, 135.

CD: [θ] −10,000 (252 nm, H$_2$O)

EXAMPLE 29

N$^6$-benzoyl2'-deoxy neplanocin A

2'-iodo-3',5'-O-(1,1,3,3-tetraisopropyl disiloxane-1,3-di-yl)-N$^6$-benzoyl neplanocin A (230 mg), a catalytic amount of azobisisobutyronitrile, and tin tributyl hydride (0.089 ml), dissolved in anhydrous benzene, were refluxed for 1 hour. The reaction mixture was concentrated in vacuo and purified by silica gel column chromatography using chloroform-ethanol (40:1) to obtain N6-benzoyl-2'-deoxy-3',5'-O-(1,1,3,3-tetraisopropyl disiloxane-1,3-di-yl) neplanocin A.

TLC: $Rf_1 = 0.30$, $Rf_4 = 0.40$

Mass: 593 (M$^{30}$), 550, 354, 316, 311, 240, 105.

(2) The product obtained hereinabove and tetrabutylammonium fluoride (100 mg) were dissolved in tetrahydrofuran (1 ml), and stirred at room temperature for 10 minutes. The reaction mixture was concentrated, charged on a TLC plate and developed by chloroform-methanol (7:1). The band showing $Rf_2 = 0.41$ was collected, extracted with chloroform-methanol (5:1), concentrated in vacuo, then treated with diethyl ether to obtain a powder of N$^6$-benzoyl-2'-deoxy neplanocin A (52 mg).

NMR: δppm (DMSO-$d_6$) 2.4 (2H, m., H-2'), 4.18 (2H, slightly broad, H-5'), 4.9–5.0 (2H, t.t., d.d., H-3' and OH-5'), 5.14 (1H, d., OH-3'), 5.82 (2H, H-6' and H-1'), 7.5–7.7 (3H, m., phenyl proton), 8.0–8.1 (2H, m., phenyl proton), 8.33 (1H, S., H-2), 8.72 (1H, S., H-8), 11.12 (1H, broad, NH).

Mass: 351 (M$^{31}$), 350, 240, 136, 135.

EXAMPLE 30

2'-(R)-acetylthio-2'-deoxy neplanocin A (1) 2'-O-trifluoromethanesulfonyl-3',5'-O-(1,1,3,3-tetraisopropyl disiloxane-1,3-di-yl) neplanocin A (1.9 g) and potassium thioacetate (0.62 g) were dissolved in hexamethylphosphoramide (20 ml) and the mixture was stirred at room temperature for 3 hours. The reaction mixture was poured into ice water. The precipitate was filtered, washed with water and again dissolved in chloroform. The solution was charged on a column of silica gel and eluted with benzene-ethyl acetate (1:2) to obtain a powder of 2'-(R)-acetylthio-2'-deoxy-3',5'-O-(1,1,3,3-tetraisopropyl disiloxane-1,3-di-yl) neplanocin A (1.55 g).

TLC: $Rf_6 = 0.19$

NMR: δppm (CED$l_3$) 1.1 (28H; isopropyl), 2.11 (3H, S., —S—COCH ), 4.38 (1H, t., H-3'), 4.46 (2H, slightly broad, H-5'), 5.38 (1H, d.d., H-2'), 5.64 (2H, slightly broad, NH$_2$, exchanged by D$_2$O), 5.75 (1H, d.d., H-1'), 5.85 (1H, J≃O, H-6'), 7.59 (1H, S., H-2), 8.28 (1H, S., H-8).

Mass: 563 (M+), 520 (M+ −43), 488, 353, 136, 135.

(2) Tetrabutylammonium fluoride (about 100 mg) was added to the above product (110 mg) dissolved in dry tetrahydrofuran (2 ml), and the mixture was stirred at room temperature for 5 minutes. The reaction mixture was concentrated in vacuo and the residue was dissolved in methanol which was immediately neutralized with aqueous acetic acid, then charged on a silica gel TLC plate. The band showing $Rf_2 = 0.23$ was collected after developing with chloroform-methanol (5:1). The extract was dried in vacuo to obtain powdery 2'-(R)-acetylthio-2'-deoxy neplanocin A (55 mg, yield: 88%).

TLC: $Rf_2 = 0.23$

UV: $\lambda_{max}^{H2O} = 262$ nm

CD: [θ] −42000 (262 nm, H$_2$O)

NMR (FX-200-FT, DMSO-$d_6$): δppm (TMS) 2.10 (3H, S., acetylthio), 4.12 (1H, d.d., H-2'), 4.16 (2H, slightly broad, H-5'), 4.91 (2H, m., OH-3' or OH-5' and H-3', changed to 1H, d. upon addition of D$_2$O), 5.61 (2H, m., OH-3' or OH-5' and H-1', changed to 1H, d. by addition of D$_2$O), 5.80 (1H, J≃O, H-6'), 7.17 (2H, slightly broad, NH$_2$-6, disappeared upon addition of D$_2$O), 7.86 (1H, S., H-2), 8.08 (1H, S., H-8).

What is claimed is:

1. 2',3',5'-O-triacetyl neplanocin A.
2. 2',3'-O-benzylidene neplanocin A.
3. N$^6$, N$^6$,5'-O-tribenzoyl neplanocin A.
4. N$^6$,5'-O-dibenzoyl neplanocin A.